United States Patent
Jungbauer et al.

(10) Patent No.: US 12,406,767 B2
(45) Date of Patent: Sep. 2, 2025

(54) METHOD FOR DOCUMENTING A REPROCESSING OF A REUSABLE MEDICAL DEVICE AND ASSEMBLY THEREFOR

(71) Applicant: OLYMPUS Winter & Ibe GmbH, Hamburg (DE)

(72) Inventors: Sebastian Jungbauer, Hamburg (DE); Sven Pabst, Giekau (DE); Hendrik Timmermann, Hamburg (DE); Andreas Mueckner, Schwarzenbek (DE)

(73) Assignee: Olympus Winter & Ibe GmbH, Hamburg (DE)

(*) Notice: Subject to any disclaimer, the term of this patent is extended or adjusted under 35 U.S.C. 154(b) by 133 days.

(21) Appl. No.: 18/386,058

(22) Filed: Nov. 1, 2023

(65) Prior Publication Data
US 2024/0290480 A1    Aug. 29, 2024

Related U.S. Application Data

(60) Provisional application No. 63/448,377, filed on Feb. 27, 2023.

(51) Int. Cl.
    *G16H 40/40*    (2018.01)
    *G01K 3/00*     (2006.01)

(52) U.S. Cl.
    CPC ............. *G16H 40/40* (2018.01); *G01K 3/005* (2013.01)

(58) Field of Classification Search
    CPC ........ G16H 40/40; G16H 15/00; G16H 40/20; G01K 3/005; G01K 3/04; G01K 1/02;
    (Continued)

(56) References Cited

U.S. PATENT DOCUMENTS

2008/0130706 A1    6/2008    Kellner et al.
2017/0348452 A1*   12/2017   Kuzelka .................. A61B 90/98

FOREIGN PATENT DOCUMENTS

CN          210986459 U    *   7/2020

OTHER PUBLICATIONS

Alfa, Michelle J. "Current issues result in a paradigm shift in reprocessing medical and surgical instruments." American Journal of Infection Control. 44(5):e41-E45 (Year: 2016).*

* cited by examiner

*Primary Examiner* — Linh Giang Le
(74) *Attorney, Agent, or Firm* — Scully, Scott, Murphy & Presser, P.C.

(57) ABSTRACT

A method for documenting a reprocessing of a reusable medical device. The reusable device comprising at least one temperature sensor configured to provide temperature data representing a temperature of the medical device, a real time clock (RTC) configured to provide timestamps and one or more processors including hardware configured to process the temperature data and the timestamps. The method includes: monitoring the temperature of the medical device during the reprocessing; and a) upon detecting the temperature exceeding a first predefined threshold, the one or more processors receiving and saving a first current timestamp provided by the RTC, and setting the one or more processors into a low-power mode, and b) upon detecting the temperature falling below a second predefined threshold, setting the one or more processors into an active mode, and the one or more processors receiving and saving a second current timestamp provided by the RTC.

19 Claims, 3 Drawing Sheets

(58) Field of Classification Search
CPC .......... G01K 13/00; A61B 90/00; A61B 1/00; A61B 1/121; A61B 90/08; A61B 90/70; A61B 2090/0813; A61B 2090/701; A61B 2560/0238; G04B 47/00
See application file for complete search history.

METHOD FOR DOCUMENTING A REPROCESSING OF A REUSABLE MEDICAL DEVICE AND ASSEMBLY THEREFOR

CROSS-REFERENCE TO RELATED APPLICATION

The present application is based upon and claims the benefit of priority from U.S. Provisional Application No. 63/448,377 filed on Feb. 27, 2023, the entire contents of which is incorporated herein by reference.

BACKGROUND

Field

The present disclosure relates to a method for documenting a reprocessing of a reusable medical device. Furthermore, the present disclosure relates to an assembly for documenting a reprocessing of a reusable medical device. Moreover, the present disclosure relates to a reusable medical device as well as a system for documenting a reprocessing of a reusable medical device.

Prior Art

Reusable medical devices, such as endoscopes or surgical instruments or hand instruments, have to be cleaned and disinfected reliably after each use. This procedure is known as "reprocessing" as the reusable medical device is prepared for another patient. Typically, such a reprocessing is performed in a reprocessing device, e.g., a washer disinfector using process chemicals or using thermal means. For example, autoclaves are used to sterilize equipment and supplies by exposing them to pressurized saturated steam at temperatures above 100° C.

Documenting the reprocessing cycles experienced by a reusable medical device can be helpful for maintenance and service. Users, manufacturers as well as workshops responsible for maintenance can deduce from the number and kind of reprocessings a medical device has undergone, e.g., how much thermal stress the device has been subjected to. This may be relevant for deciding when it is time to call the medical device for regular maintenance, e.g. to replace wear parts that need to be replaced regularly.

It is known for reusable medical devices suitable for reprocessing in washer disinfectors that they may comprise a counter that counts how many times the device has been plugged into such a cleaning system. While some types of reprocessing only require plugging in once, other types of reprocessing require repeated cycles of plugging in and unplugging. This may cause multiple counts for one reprocessing.

Furthermore, reprocessing devices, such as washer disinfectors, may be configured to keep track of the reprocessing processes performed. It involves a considerable administrative effort to ensure that the type of reprocessing and the reprocessed medical device are reliably assigned to each other. In addition, the information per se is only available on the reprocessing device and not on the reusable medical device.

SUMMARY

An object is to document reliable and efficient reprocessing of a reusable medical device, such as for usage for service and maintenance of the reusable medical device.

Such object can be solved by a method for documenting a reprocessing of a reusable medical device, the reusable device comprising at least one temperature sensor configured to provide temperature data representing a temperature of the medical device, a real time clock (RTC) configured to provide timestamps and a documentation unit (a processor comprising hardware) configured to process the at least one temperature sensor's temperature data and the RTC's timestamps, wherein the method comprises monitoring the temperature of the medical device during the reprocessing and a) upon detecting a temperature exceeding a first predefined threshold, the documentation unit receiving and saving a current timestamp provided by the RTC, the documentation unit thereafter being set into a low-power mode, and b) upon detecting the temperature falling below a second predefined threshold, setting the documentation unit into an active mode, and the documentation unit receiving and saving a current timestamp provided by the RTC.

In order to determine the condition of a medical device, e.g. before or during maintenance, information on the duration and temperatures of reprocessing to which the medical device has been exposed can be used. According to the presently disclosed method, this can be achieved by the medical device having a documentation unit that can comprise or be implemented by a microprocessor, a field programmable gate array (FPGA) or the like, documenting at which points in the process of a reprocessing certain temperature thresholds were crossed, thereby providing the medical device itself with a simple configuration to evaluate the duration of reprocessing. This has not been considered earlier, since the power consumption of a microprocessor or an FPGA increases significantly at higher temperatures. However, most of the integrated circuit comprising the documentation unit can be powered down, except for very few essential components, for as long as a predefined temperature threshold is exceeded. Meanwhile, a real time clock and a temperature sensor triggering an end to the low-power phase remain functional. During this low-power phase at high temperatures, single data points of time and temperature can be measured and buffered, i.e. temporarily saved. When a temperature indicating the end of a reprocessing is detected, the documentation unit can be powered back up into an active mode, ready for saving, processing and communicating the data.

A reusable medical device can be one of an endoscope, a video endoscope, a surgical instrument and a hand instrument. For example, reprocessing of such a device can be performed using a washer disinfector.

The documentation unit can be or can comprise an integrated circuit, such as a microcontroller, a field programmable gate array (FPGA) or a configurable mixed-signal integrated circuit (CMIC) such as a GreenPAK™ device by Renesas Electronics. The reusable medical device can comprise at least one temperature sensor; in embodiments, the reusable medical device can comprise at least two temperature sensors, such as two, three, four or more temperature sensors. Each temperature sensor can be linked to a predefined threshold specific to this temperature sensor, wherein the respective temperature sensor can trigger a trigger command upon detecting the temperature exceeding or falling below its threshold.

Such a trigger command can be a command sent to the documentation unit, e.g. setting the documentation unit into a low-power mode or into an active mode. The low-power mode can be an ultra-deep sleep mode, wherein all nonessential functional units of the documentation unit can be deactivated for saving power. In low-power mode, the documentation unit can run with lowest possible power consumption as priority. A low-power mode can be characterized by a low quiescent current used by the documentation unit. Any peripheral equipment can be deactivated and/or a number of universal asynchronous receiver transmitters (UART) can be deactivated. In another embodiment, the documentation unit can be switched off in low-power mode, such as by using a semiconductor switch. In active mode, the documentation unit can run with a best availability of functions as priority.

In an embodiment, in which the documentation unit can comprise the RTC, the RTC can remain functional, even if the documentation unit is set into a low-power mode.

In a further embodiment, the RTC can be configured to buffer at least one timestamp, wherein step (b) can further comprise the documentation unit saving at least one timestamp buffered by the RTC. For buffering at least one timestamp, the RTC can comprise a buffer unit. Buffering a timestamp can correspond to saving a timestamp temporarily before it is received and saved by the documentation unit. Buffering a timestamp can be conducted with the lowest possible energy consumption. Buffering can allow for storing at least one timestamp while the documentation unit is set into low-power mode, improving the precision of the documentation of the reprocessing.

For an efficient documentation of the reprocessing, it can be desired to associate thresholds with the corresponding timestamps received in step (a) and step (b) as well as timestamps buffered while the documentation unit is in the low-power mode. In embodiments, the documentation unit can be configured to associate the timestamps with the first predefined threshold, the second predefined threshold and any further predefined thresholds.

When preparing the reusable device for the method, the predefined thresholds can be implemented to both the at least one temperature sensor and the documentation unit. This can be used where the approximate temperature curve of the reprocessing is known. Then, the documentation unit can sort the timestamps chronologically and match the corresponding predefined thresholds based on the known approximate temperature curve of the reprocessing in the expected order.

In a further embodiment, between step (a) and step (b) an additional step (b1) can be performed, comprising upon detecting the temperature exceeding a third predefined threshold, the third predefined threshold being higher than the first predefined threshold, buffering a current timestamp provided by the RTC. Acquiring at least one additional timestamp corresponding to a predefined temperature can allow for a more precise documentation of the reprocessing.

In another embodiment, between step (a) and step (b) at least one additional step (b1) can be performed, comprising, upon detecting the temperature exceeding at least one third predefined threshold, the at least one third predefined threshold being higher than the first predefined threshold, the RTC providing and buffering a current timestamp. With this, timestamps can be provided and buffered on a rising flank of the reprocessing temperature curve, to be recorded by the documentation unit after it has been powered back up.

Multiple steps of (b1), each buffering a current timestamp when at least one of multiple third predefined thresholds is exceeded, can allow for a more precise documentation of the reprocessing, allowing the rising flank of the reprocessing temperature curve to be mapped at multiple temperature values, which can correspond to different programs or steps in the reprocessing process. In this embodiment, there can be more than one third predefined threshold. E.g., if step (a) is performed when a temperature of 60° C. is exceeded, a first step (b1) can buffer the current timestamp when exceeding a first third threshold of 80° C. and a second step (b1) can buffer the current timestamp when exceeding a second third threshold of 110° C. The multiple (b1) thresholds can also be used to distinguish between different reprocessing programs, some of which can only exceed a lower temperature threshold and others can exceed even higher temperature thresholds.

For associating thresholds with the corresponding timestamp, the buffer unit of the RTC can comprise at least one buffer slot for buffering one timestamp per slot and, when preparing the reusable device for the method, the predefined thresholds can be implemented to the at least one temperature sensor, wherein each predefined threshold except for the thresholds of step (a) and step (b) can be assigned one or more buffer slots. Upon detecting the exceeding or the falling below the temperature of a given threshold, the RTC can provide and buffer a current timestamp in the specific buffer slot assigned to the corresponding threshold. In this embodiment, when preparing the reusable device for the method, the documentation unit can be supplied with information of the buffer slots and their corresponding thresholds. For example, the documentation unit can be supplied with the information of the thresholds of at least one temperature sensor together with the information, which threshold can be assigned to which buffer slot. Hence, the documentation unit can be configured to associate predefined thresholds with corresponding buffer slots of the buffer unit. When saving the timestamps in step (b), the timestamps can be associated with the corresponding predefined thresholds corresponding to the buffer slots.

In another embodiment, the buffer can be configured to comprise subsequent slots to be filled with subsequently provided timestamps accompanied by an indicator of the threshold or temperature sensor that prompted the RTC to provide the timestamp. The readout of the buffer can then provide the buffered timestamps along with the indicator of the threshold or temperature sensor.

In a further embodiment, between step (a) and step (b) an additional step (b2) can be performed, comprising, upon detecting the temperature falling below a fourth predefined threshold, the fourth predefined threshold being set at a higher temperature than the second predefined threshold, buffering a current timestamp provided by the RTC. Acquiring additional time and temperature data of the reprocessing can allow for a more precise documentation.

In another embodiment, between step (a) and step (b) at least one additional step (b2) can be performed, comprising, upon detecting the temperature falling below at least one fourth predefined threshold, the at least one fourth predefined threshold being set at a higher temperature than the second predefined threshold, the RTC providing and buffering a current timestamp. With this, timestamps can be provided and buffered on a falling flank of the reprocessing temperature curve, to be recorded by the documentation unit after it has been powered back up. This can also allow for a more precise and granular documentation of the reprocessing. In this embodiment, there can be more than one fourth predefined threshold. E.g., if step (b) is performed when the temperature of the medical device has fallen below of 40° C., a first step (b2) can buffer the current timestamp when falling below a first fourth threshold of 100° C. and a second step (b2) can buffer the current timestamp when falling below a second fourth threshold of 70° C.

An additional step (b1) and an additional step (b2) can be performed in any order, i.e. a step (b1) can be performed before a step (b2) and a step (b2) can be performed before a step (b1), depending on the temperature curve of a reprocessing program. At least one third threshold can be the same as at least one fourth threshold. This can allow for a documentation of the time duration the temperature has exceeded this temperature threshold.

Multiple steps of (b2), each buffering a current timestamp when at least one of multiple fourth predefined threshold is exceeded, can allow for a more precise documentation of the reprocessing, allowing the falling flank of the reprocessing temperature curve to be mapped at multiple temperature values, which can correspond to different programs or steps in the reprocessing process. In this embodiment, there can be more than one fourth predefined threshold. E.g., if step (b) is performed when the temperature has fallen below 40° C., a first step (b2) can buffer the current timestamp when falling below a first fourth threshold of 100° C. and a second step (b2) can buffer the current timestamp when falling below a second fourth threshold of 60° C. The multiple (b2) thresholds can also be used to distinguish between different reprocessing programs, some of which can only fall below a lower temperature threshold and others can also fall below higher temperature thresholds, depending on the reprocessing program's highest temperature.

In a further embodiment, in step (b2) the RTC providing and buffering a current timestamp can require fulfilling the additional condition that the time elapsed since step (a) has exceeded a predefined waiting time interval. This can allow for a more accurate documentation of the reprocessing, as possible fluctuations in temperatures can be ruled out. Furthermore, this can save power, as the additional time condition can allow to minimize the number of buffered timestamps necessary.

In other embodiments, in step (b2) the RTC providing and buffering a current timestamp can require fulfilling the additional condition but the time elapsed since a predefined step (b1) or another predefined step (b2) has exceeded a predefined waiting time interval. This can also allow for a more controlled documentation of the reprocessing.

In a further embodiment, in step (a), the detecting of the temperature exceeding a first predefined threshold can be performed by a first temperature sensor and in step (b) the detecting the temperature falling below a second predefined threshold by the first temperature sensor or a second temperature sensor. This can hold the advantage of low power consumption and simple construction of the temperature sensors.

Each additional step (b1) or (b2) can be performed by a separate temperature sensor. Thus, the medical device can comprise as many temperature sensors as steps (a), (b), (b1) and (b2) are comprised by the method. In other embodiments, multiple steps can be performed by the same temperature sensor, e.g., a temperature sensor can be configured to perform a step (b1) and a step (b2) for thresholds of the same predefined temperature. In another embodiment, a temperature sensor can be configured to perform an additional step (b1) or an additional step (b2) multiple times, i.e. to buffer a current timestamp multiple times, if the predefined threshold is exceeded or fallen below more than once.

In a further embodiment, the method can comprise a step (c), comprising reading out the saved timestamps and the corresponding thresholds from the documentation unit. A read out can allow for a more efficient analysis of the documentation of the reprocessing as well as for comparisons between the reprocessing of different devices and for archiving the documentation effectively. Step (c) can be performed during maintenance, service or repair or in regular use, e.g. on a regular basis, such as by the user of the medical device, e.g. every day, every week or every month. In embodiments, step (c) can be performed using a wire-bound connection or can be performed using a wireless connection.

In another embodiment, a step (c) can comprise reading out the saved timestamps from the documentation unit. In this embodiment, the corresponding temperature thresholds can be documented separately, e.g. the temperature thresholds can be default temperature thresholds predefined by the manufacture of the medical device.

In a further embodiment, the method can comprise a step (d), comprising analyzing the saved timestamps with the corresponding thresholds and identifying the reprocessing applied to the medical device. An analysis of the reprocessing of the device can allow for a better understanding of the current condition of the medical device, for example indicating necessary maintenance or recommended replacement of wear parts. In a simple form of analysis, step (d), e.g., allows to determine the number of reprocessings a medical device has undergone.

In an embodiment, step (d) can comprises identifying the process of reprocessing applied to the medical device as reprocessing by treatment with process chemistry or as reprocessing by an autoclave.

Step (c) and step (d) can be subsequent steps, wherein the step (d) can follow step (c) or wherein step (c) can follow step (d). Step (d), i.e. the analysis step, can be performed by the documentation unit or can be performed by an external data processing device. Step (d) can be performed during maintenance or service or can be performed during regular use of the medical device.

In an embodiment, step (d) can comprise calculating a time interval of reprocessing duration by subtracting the timestamp of step (b) and the timestamp of step (a). This way a reprocessing duration time difference $\Delta t$ can be obtained. Advantageously, step (d) can comprise calculating more than one difference between timestamps saved by the documentation unit. This can include all timestamps buffered in steps (b1) or steps (b2) and saved in step (b).

In an embodiment, the method can comprise performing multiple cycles of steps (a) and (b), such as including additional steps (b1) and/or (b2) in between, and subsequently performing one step (c) and/or one step (d).

Step (d) can be performed or supported by a computer-based decision support system (CDSS) for supporting identifying the reprocessing applied to the medical device. The CDSS can be configured to process input parameters by an artificial intelligence (AI) model and to generate a predicted output.

The object can also be solved by an assembly for documenting a reprocessing of a reusable medical device, comprising at least one temperature sensor configured to provide temperature data representing a temperature of the medical device, a real time clock (RTC) configured to provide timestamps and a documentation unit configured to process documentation data including the at least one temperature sensor's temperature data and the RTC's timestamps, wherein the documentation unit comprises a memory for saving documentation data, wherein the documentation unit is configured to run in active mode or in low-power mode, wherein the at least one temperature sensor is configured to send a trigger command to the documentation unit if the temperature is exceeding or falling below a predefined threshold and the documentation unit comprises a command interface configured to receive a trigger command from a temperature sensor. Such an assembly can allow for implementing the method described above in a medical device.

The assembly, which can also be called an apparatus within the context of the present disclosure, can be an embedded system. The assembly can comprise at least two, at least three or at least four temperature sensors. This can be useful, if the assembly is configured to perform additional steps (b1) or (b2).

The documentation unit can be an integrated circuit. A low-power mode of the documentation unit can be an ultra-deep sleep mode as described above. A trigger command sent from a temperature sensor to the documentation unit can be, e.g., a command to set the documentation unit into active mode, to set the documentation unit into low-power mode, or to save the current timestamp.

A command interface can be a computer hardware device, such as a part of an integrated circuit, configured to receive and/or transmit commands. In an embodiment, the command interface can be an interface allowing for serial communication, such as a universal asynchronous receiver-transmitter (UART).

In a further embodiment, the documentation unit can comprise a microcontroller or a field programmable gate array (FPGA) or a configurable mixed-signal integrated circuit (CMIC). The documentation unit can be an integrated circuit. Using a microcontroller can allow for more functions, such as wireless communication capabilities of the documentation unit, which can allow for a permanent supervision of the documentation unit. A field programmable gate array can hold the advantage of low power consumption and simple implementation. In an embodiment, a CMIC can be a GreenPAK™ device by Renesas Electronics.

In an embodiment, the assembly and/or the documentation unit can be an Internet of Things device.

In a further embodiment, the RTC can be configured to receive a trigger command from at least one of the temperature sensors and to buffer a current timestamp signal. In such an embodiment, at least one of the temperature sensors can be configured to send a trigger command to the RTC to buffer a current timestamp signal. The RTC can be configured to buffer multiple timestamps.

In a further embodiment, the documentation unit can comprise the RTC or the RTC can be a separate device from the documentation unit. Separate device can mean that the RTC is not an integral compound of the documentation unit. This can allow for lower power consumption, especially when the documentation unit is set into low-power mode. A documentation unit comprising the RTC can hold the advantage of a cost-efficient and simple configuration of the assembly. If the documentation unit comprises the RTC, the RTC can remain functional in low-power mode, as the RTC is between step (a) and step (b) of the above-described method.

In a further embodiment, a first temperature sensor can be configured to send a trigger command to the documentation unit if the temperature is exceeding a first predefined threshold and the first temperature sensor or a second temperature sensor can be configured to send a trigger command to the documentation unit if the temperature is falling below a second predefined threshold. Using two separate temperature sensors for detecting the temperature threshold for setting the documentation unit into low-power mode and into active mode, can allow for a reliable use of the assembly and therefore reliable performance of the method as well as cost efficient configuration of the integrated circuit of the documentation unit.

In embodiments, the assembly can comprise a third temperature sensor configured to send a trigger command to the RTC to buffer a current timestamp signal if the temperature is exceeding a third predefined threshold and/or a fourth temperature sensor can be configured to send a trigger command to the RTC to buffer a current timestamp signal if the temperature is falling below a fourth predefined threshold.

In a further embodiment, each of the at least one temperature sensor can be one of a temperature switch, a mechanical temperature sensor, an electrical temperature sensor and an integrated circuit temperature sensor. A temperature switch can have the advantage of a simple configuration, a mechanical temperature sensor and an electrical temperature sensor can have the advantage of low power consumption and an integrated circuit temperature sensor can have the advantage of high flexibility concerning use, e.g., use for multiple thresholds. In an embodiment, each temperature sensor can be assigned a threshold for triggering the documentation unit or for triggering the RTC upon detecting a temperature exceeding and/or falling below the threshold. Each temperature sensor can be configured to detect a temperature both exceeding or falling below the threshold as well as detecting a temperature exceeding and falling below the threshold.

In a further embodiment, the documentation unit can comprise a communication interface for transmitting documentation data to an external data processing device. As for method step (c), as described above, this can allow for a more reliable and efficient documentation of the reprocessing of the medical device. The external data processing device can be a reprocessing device, such as a washer disinfector or an autoclave. In another embodiment, the external data processing device can be a computer or a server acting as a medical device management system. In other embodiments, e.g., if the documentation unit comprises an FPGA, the external data processing device can be a specific handheld electronic device for reading out the medical device documentation unit which itself is connected to a computer. The latter embodiment can be useful for transmitting documentation data during service or maintenance.

In an embodiment, the communication interface can be configured for wire-bound communication or can be configured for wireless communication. For example, the communication interface can be a USB interface, a UART interface or a wireless local area network controller.

In a further embodiment, the external data processing device can be a network device connected to the internet. This way a continuous documentation and supervision of the reprocessing of the medical device can be possible. The network device connected to the internet can be a server based processing system. The assembly can be an Internet of Things device.

For this embodiment, the documentation unit can comprise a microcontroller. This can enhance the capabilities of the documentation unit in order to communicate with an external computer system, enabling simple communication even outside of a setting of maintenance or repair.

In a further embodiment, the documentation unit can be configured to analyze saved timestamps and the corresponding thresholds and to identify the reprocessing applied to the medical device. Such an analysis can allow for a better understanding of the status of the medical device and the reprocessing that has been performed.

In an embodiment, the documentation unit can be configured to identify the reprocessing applied to the medical device as reprocessing by treatment with process chemistry or reprocessing by an autoclave.

In another embodiment, the external data processing device can be configured to analyze saved timestamps and the corresponding thresholds and to identify the reprocessing applied to the medical device.

The external data processing device can comprise a computer-based decision support system (CDSS) for supporting identifying the reprocessing applied to the medical device. In an embodiment, the CDSS can be configured to process input parameters by an artificial intelligence (AI) model and to generate a predicted output. The predicted output can comprise the type of reprocessing applied to the medical device.

In a further embodiment, the assembly can be configured to carry out a method as described above.

Such object can also be solved by a reusable medical device comprising an assembly as described above.

Such object can furthermore be solved by a system for documenting a reprocessing of a reusable medical device, comprising a reusable medical device as described above and a reprocessing device for reprocessing the reusable medical device and an external data processing device. By using such a system, the whole process of reprocessing the medical device and documenting the reprocessing can be performed efficiently and reliably.

The above-described method as well as the assembly, the reusable medical device and the system constitute several embodiments. The assembly, the medical device, the system, and its constituents are set up to incorporate the above-described method with all its embodiments. The method can be incorporated using the above-described components of the assembly, of the reusable medical device or the system.

BRIEF DESCRIPTION OF THE DRAWINGS

Further features will become apparent from the description of the embodiments together with the claims and the included drawings. Embodiments can fulfill individual characteristics or a combination of several characteristics.

The embodiments are described below, without restricting the general intent of the invention, based on exemplary embodiments, wherein reference is made expressly to the drawings with regard to the disclosure of all details that are not explained in greater detail in the text. In the drawings.

DETAILED DESCRIPTION

Figure 1:
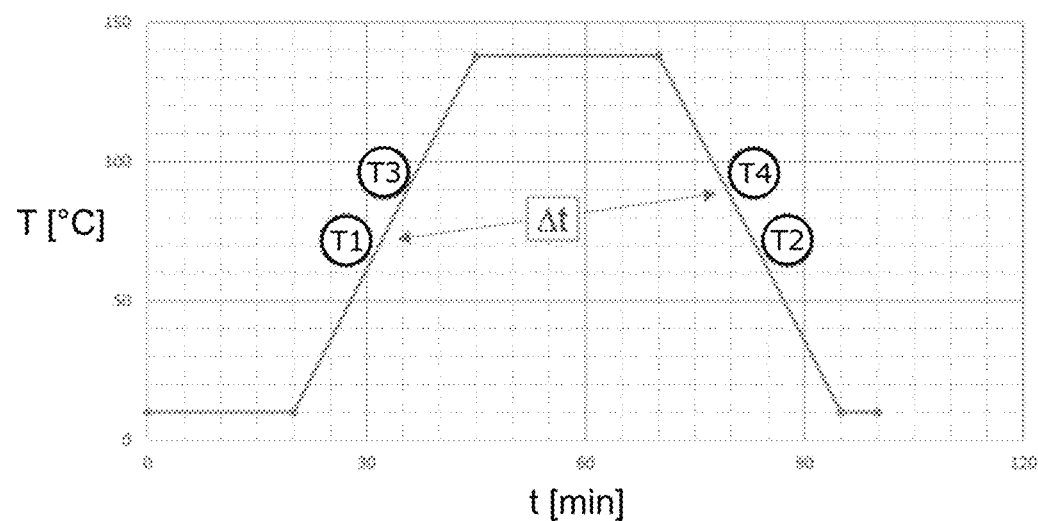
FIG. 1 illustrates a schematic diagram of temperature T vs. time t during a first embodiment of a reprocessing of a reusable medical device.

FIG. 1 shows a schematic diagram of the temperature T during the course of a first embodiment of a reprocessing of a reusable medical device 91. In this embodiment, the reprocessing is a thermal reprocessing in an autoclave of an endoscope. On the horizontal axis, the time t is plotted in the unit of minutes. Around 20 minutes after the start of the reprocessing, the temperature T of the endoscope increases up to a constant level of T=140° C., where the medical device remains for 30 minutes. Subsequently, the temperature declines continuously down to the original temperature of 10° C., which is reached after 100 minutes after the start of the reprocessing.

For this embodiment of a reprocessing, for the documentation the threshold of the temperature of the medical device 91 are predefined as exceeding 60° C. (threshold 1, T1), falling below 55° C. (threshold 2, T2), exceeding 90° C. (threshold 3, T3) and falling below 85° C. (threshold 4, T4). Here, T1 and T2 as well as T3 and T4 are set with a temperature difference of 5 Kelvin each, thereby introducing a hysteresis in the temperature-dependent response of the system. In other embodiments, T1 and T2 and/or T3 and T4 may be predefined at different temperatures or, respectively, at the same temperature.

Figure 2:
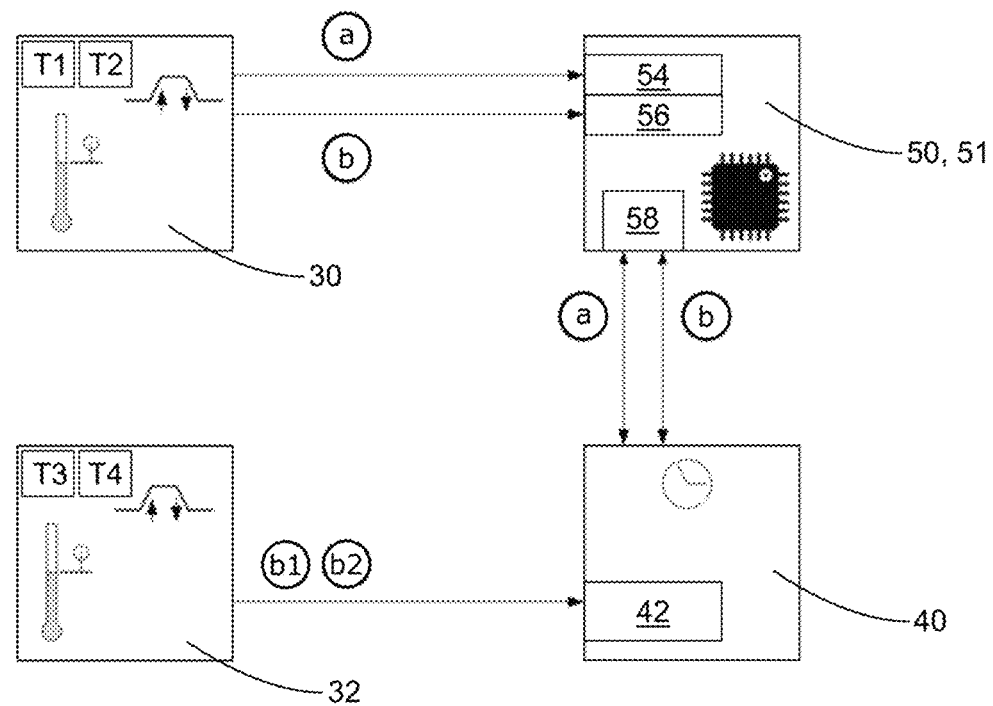
FIG. 2 illustrates a schematic view of an embodiment of a method for documenting the first embodiment of a reprocessing of a reusable medical device.

FIG. 2 shows a schematic view of an embodiment of a method for documenting the first embodiment of a reprocessing of a usable medical device 91. FIG. 2 explains how a reprocessing as presented in FIG. 1 is documented using the method according to an embodiment. A first temperature sensor 30 monitors the temperature of the medical device 91 and upon detecting the temperature exceeding a first threshold T1, in this case 60° C., the first temperature sensor 30 triggers the documentation unit 50. In this embodiment, the documentation unit 50 is a microcontroller 51. The documentation unit 50 receives the trigger command from the first temperature sensor 30 and according to method step (a) (S210) receives and saves 58 a timestamp from the real time clock (RTC) 40. Subsequently, the documentation unit 50 is set into a low-power mode 54.

In the further course of the reprocessing, the temperature of 90° C. is exceeded, so that a second temperature sensor 32 detects that the third threshold T3 is exceeded and, thus, triggers the real time clock 40 to buffer a timestamp 42. This is an embodiment of a step (b1) (S220).

The reprocessing continues, including a temperature rising to its maximum. Upon falling below the fourth threshold T4 the second temperature sensor 32 triggers again the RTC 40 to buffer 42 another timestamp. This is an embodiment of a step (b2) (S230).

The next step (b) (S240) is performed when the first temperature sensor 30 detects that the temperature of the medical device 91 has fallen below the second threshold T2. The first temperature sensor 30 triggers the documentation unit 50 to set 56 the documentation unit 50 into an active mode and subsequently to receive and save 58 a timestamp from the RTC 40. Furthermore, the documentation unit 50 saves any timestamps buffered by the RTC 40, i.e. both timestamps buffered in step (b1) and step (b2) for thresholds T3 and T4.

In the embodiment shown in FIG. 2, the thresholds T3 and T4 are detected by the same temperature sensor, the second temperature sensor 32. In another embodiment, both thresholds T3 and T4 may be detected by separate temperature sensors. The same holds for the thresholds detected by the first temperature sensor 30.

Figures 3, 4A, 4B, 4C, 4D:
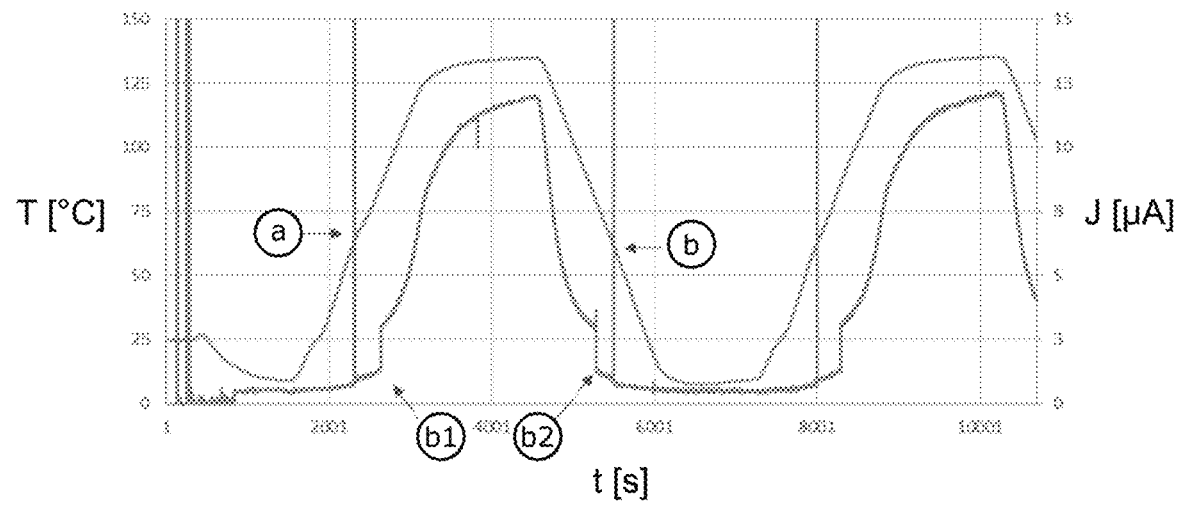
FIG. 3 illustrates a diagram of temperature T and current J vs. time t during an experimental reprocessing of a reusable medical device.
FIG. 4a-4d illustrate four block diagrams of four other embodiments of a method for documenting a reprocessing of a reusable medical device.

FIG. 3 shows a diagram of temperature T and current J against the time t during an experimental reprocessing of a reusable medical device 91. The reprocessing follows the temperature curve as depicted in FIG. 1, wherein for the data shown in FIG. 3 the reprocessing cycle is performed twice.

The graph shows that for step (a) (S210) and step (b) (S230), i.e. when exceeding T1 and falling below T2, the current J used by the assembly 80 including the documentation unit 50 shows a high spike of more than 15 µA. At these moments, power consumption is increased, as the documentation unit 50 is set into low-power mode or active mode, respectively.

Other than that, FIG. 3 shows the effect of the method of documenting the reprocessing of a medical device 91, because the current J is kept at low currents smaller than 15 µA despite the high temperatures within the medical device 91. The sudden increase of the current J at step (b1) and the sudden decrease of the current J at step (b2) are due to the use of an open-drain output in the second temperature sensor 32 detecting the temperature thresholds T3 and T4. Other types of temperature sensors, e.g. a push-pull output temperature sensor, may be used. A push-pull output allows for even smaller power consumption.

After setting the documentation unit 50 into an active mode in step (b) (S240), in this embodiment the method comprises step (d) (S260), so that the saved timestamps and the corresponding thresholds are analyzed. The documentation unit 50 calculates the time difference between the timestamps, including $\Delta t$ as time difference between the timestamps of steps (b2) (S230) and step (a) (S210) as depicted in FIG. 1.

FIG. 4 depicts four block diagrams of four other embodiments of a method for documenting a reprocessing of a reusable medical device. An embodiment of such a method would comprise a step (a) (S210) and a step (b) (S240). Another embodiment comprises an additional step (b2) (S230) between step (a) (S210) and step (b) (S240).

FIG. 4a shows an exemplary method comprising subsequent step (a) (S210.1), step (b1) (S220.1), two steps (b2) (S230.1, S230.2) and a step (b) (S240.1). The two steps (b2) (S230.1, S230.2) have different predefined thresholds, so that more information about the reprocessing is documented.

FIG. 4b describes a method comprising two steps (b1) (S220.2, S220.3) as well as two steps (b2) (S230.3, S230.4). The temperature thresholds differ from the steps already presented in FIG. 4a. After setting the documentation unit 50 into active mode in step (b) (S240), step (d) (S260) and step (c) (S250) are performed.

FIG. 4c distinguishes itself from the previous examples by mixing subsequent steps (b1) and steps (b2). After a step (b1) (S220.4) and a step (b2) (S230.5), another step (b1) (S220.5) and step (b2) (S230.6) are performed. This may be useful if the temperature increases and decreases multiple times during a specific type reprocessing. In the end of the method described in FIG. 4c step (c) (S250) and step (d) (S260) are performed.

FIG. 4d depicts an embodiment of the method without a step (b1) (S220).

Figure 5:
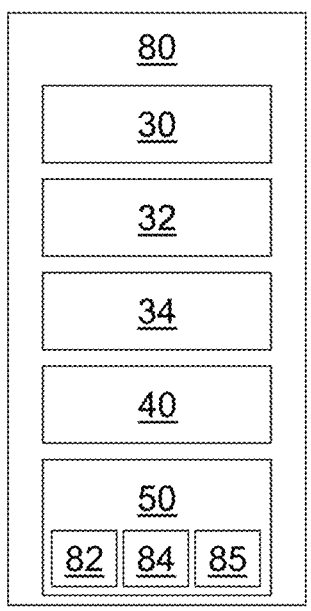
FIG. 5 illustrates a schematic view of a first embodiment of an assembly for documenting a reprocessing of a reusable medical device.

FIG. 5 shows a schematic view of a first embodiment of an assembly 80 for documenting a reprocessing of a usable medical device 91. An assembly 80 comprises a first temperature sensor 30, a second temperature sensor 32, a third temperature sensor 34, an RTC 40, a documentation unit 50, wherein the documentation unit 50 is a microcontroller 51 and comprises a memory 82, a command interface 84 and a communication interface 85. The communication interface 85 may be a wireless local area network interface.

Figure 6:
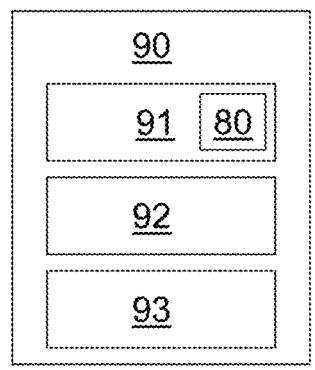
FIG. 6 illustrates a schematic view of a first embodiment of a system for documenting a reprocessing of a reusable medical device.

FIG. 6 shows a schematic view of a first embodiment of a system 90 for documenting a reprocessing of a reusable medical device 91, wherein the system 90 comprises a reusable medical device 91, comprising an assembly 80, as well as a reprocessing device 92 and an external data processing device 93. In this embodiment the reusable medical device 91 is a video endoscope, the reprocessing device 92 may be a washer disinfector, and the external data processing device 93 is a controller of the video endoscope.

Figure 7:
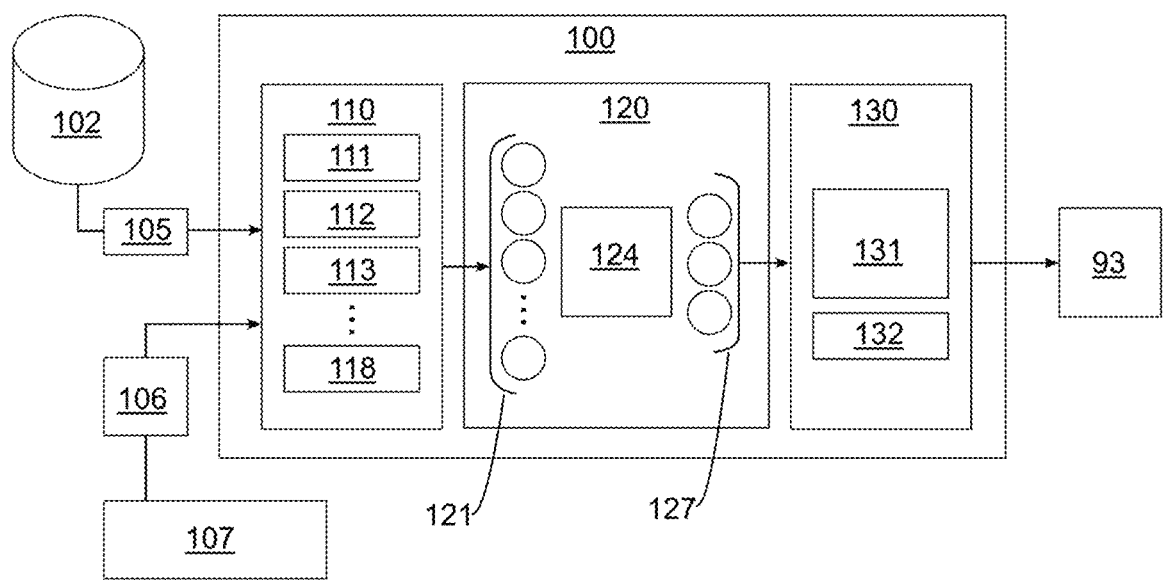
FIG. 7 illustrates a schematic view of steps performed by a computer-based decision support system.

FIG. 7 shows a schematic view of steps performed by a computer-based decision support system (CDSS) 100 that is configured to identify the reprocessing applied to the medical device on input parameters 121. In various embodiments, the CDSS 100 includes an input interface 110 through which input parameters based upon predefined reprocessing data 105 and additional input data 106 from additional input data sources 107, such as the documentation unit 50, which are specific to the reprocessed medical device are provided as input features to an artificial intelligence (AI) model 120, a processor which performs an inference operation in which the input parameters are applied to the AI model to generate a predicted output 131, such as the reprocessing applied to the medical device, and an output interface 130 through which the predicted output 131, including confidence score (s) 132, is communicated to a user, e.g. medical staff or a service technician, or to the documentation unit 50 or an external data processing device 93.

In some embodiments, the input interface 110 may be a direct data link between the CDSS 100 and one or more data sources 102, 107 that generate at least some of the input features. For example, the input interface 110 may transmit timestamps and/or thresholds directly to the CDSS during a reprocessing identification procedure. Additionally, or alternatively, the input interface 110 may be a classical user interface that facilitates interaction between a user and the CDSS 100. For example, the input interface 110 may facilitate a user interface through which the user may manually enter timestamps and/or thresholds of the temperature of the medical device. Additionally, or alternatively, the input interface 110 may provide the CDSS 100 with access to a reprocessing type database 102 providing predefined reprocessing data, which is general data about different types of reprocessing such as their duration and temperature profile, from which one or more input features may be extracted. In any of these cases, the input interface 110 is configured to collect one or more of the following input features in association with a specific medical device on or before a time at which the CDSS 100 is used to identify the reprocessing applied to the medical device. The input features (111, 112, 113, ..., 118) may be parameters such as timestamps, thresholds, further saved temperature data, type of medical device. In other embodiments, the input interface 110 of the CDSS 100 furthermore includes other input parameters.

Based on one or more of the above input features, the processor performs an inference operation using the AI model 120 to generate the predicted output 131. For example, input interface 110 may deliver the input parameters 121 of timestamps saved or buffered in a step (a), a step (b), a step (b1) and two steps (b2) including the corresponding thresholds into an input layer 121 of the AI model 120, which propagates these input features through the AI model 120 to an output layer 127. The AI model 120 can provide a computer system the ability to perform tasks, without explicitly being programmed, by making inferences based on patterns found in the analysis of data. AI model 120 explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model 120 may be trained continuously or periodically prior to performance of the inference operation by the processor. Then, during the inference operation, the input features specific to the reprocessing may be provided to the AI model 120 and may be propagated from an input layer 121, through one or more hidden layers 124, and ultimately to an output layer 127 that corresponds to the predicted output 131. For example, if various medical devices of a specific model type have shown a similar profile of timestamps for a given set of thresholds for a given type of reprocessing, this information is included for the identification of the reprocessing applied to this specific model type of medical device.

During and/or subsequent to the inference operation, the predicted output 131 may be communicated to the user via a user interface and/or automatically be transmitted to the documentation unit 50 or an external data processing device 93. For example, if the CDSS determines that the reprocessing of the medical device is a specific type of reprocessing, this information is stored on the documentation unit 50 or on the external data processing device 93, so that this procedure of reprocessing is reliably documented.

In the drawings, the same or similar types of elements or respectively corresponding parts are provided with the same reference numbers in order to prevent the item from needing to be reintroduced.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES 30, 32, 34 temperature sensor
40 real time clock (RTC)
42 buffering a timestamp
50 documentation unit
51 microcontroller
54 setting into a low-power mode
56 setting into an active mode
58 receiving and saving a timestamp
80 assembly
82 memory
84 command interface
85 communication interface
90 system
91 reusable medical device
92 reprocessing device
93 external data processing device
100 computer-based decision support system (CDSS)
102 reprocessing types database
105 device management data
106 additional input data
107 additional input data source(s)
110 input interface
111 first input feature
112 second input feature
113 third input feature
118 n-th input feature
120 AI model
121 input layer
124 hidden layers
127 output layer
130 output interface
131 predicted output
132 confidence score(s)
S210 step (a)
S220 step (b1)
S230 step (b2)
S240 step (b)
S250 step (c)
S260 step (d)
T1 first threshold
T2 second threshold
T3 third threshold
T4 fourth threshold
t time
T temperature J current
Δt time difference

What is claimed is:

1. A method for documenting a reprocessing of a reusable medical device, the reusable device comprising at least one temperature sensor configured to provide temperature data representing a temperature of the medical device, a real time clock (RTC) configured to provide timestamps and one or more processors comprising hardware configured to process the temperature data and the timestamps, wherein the method comprises:
monitoring the temperature of the medical device during the reprocessing; and
a) upon detecting the temperature exceeding a first predefined threshold, the one or more processors receiving and saving a first current timestamp provided by the RTC, and setting the one or more processors into a low-power mode, and
b) upon detecting the temperature falling below a second predefined threshold, setting the one or more processors into an active mode, and the one or more processors receiving and saving a second current timestamp provided by the RTC.

2. The method according to claim 1, characterized in that the RTC is configured to buffer at least one of the first timestamp and the second timestamp, wherein step (b) further comprises the documentation unit saving at least one of the first and second timestamps buffered by the RTC.

3. The method according to claim 2, further comprising, between (a) and (b), upon detecting the temperature exceeding a third predefined threshold, the third predefined threshold being higher than the first predefined threshold, the RTC providing and buffering a third current timestamp.

4. The method according to claim 2, further comprising between (a) and (b), upon detecting the temperature falling below a third predefined threshold, the third predefined threshold being set at a higher temperature than the second predefined threshold, the RTC providing and buffering a third current timestamp.

5. The method according to claim 4, wherein the RTC providing and buffering a first, second or third current timestamp comprises fulfilling the additional condition that the time elapsed since (a) has exceeded a predefined waiting time interval.

6. The method according to claim 1, wherein in (a), the detecting of the temperature exceeding a first predefined threshold is performed by a first temperature sensor and in (b) the detecting the temperature falling below a second predefined threshold is performed by the first temperature sensor or a second temperature sensor.

7. The method according to claim 1, further comprising (c) reading out the saved first and current timestamp and corresponding first and second predefined threshold from the one or more processors.

8. The method according to claim 1, further comprising (d), analysing the saved first and second current timestamps with the corresponding first and second predefined thresholds and identifying the reprocessing applied to the medical device.

9. An assembly for documenting a reprocessing of a reusable medical device, the assembly comprising:
at least one temperature sensor configured to provide temperature data representing a temperature of the medical device and to output a trigger command if the temperature of the medical device is determined to one or more of exceed or fall below a predefined threshold,
a real time clock (RTC) configured to provide timestamps;
a memory for saving documentation data; and
one or more processors configured to:
process documentation data including the temperature data and the timestamps;
receive the trigger command; and
run in an active mode or in a low-power mode based on the received trigger signal; and
from the at least one temperature sensor.

10. The assembly according to claim 9, wherein the one or more processors comprise one of a microcontroller, a field programmable gate array, or a configurable mixed-signal integrated circuit.

11. The assembly according to claim 9, wherein the RTC is configured to receive the trigger command from the at least one temperature sensors and to buffer a current timestamp signal.

12. The assembly according to claim 9, wherein the one or more processors comprise the RTC or the RTC is a separate device from the one or more processors.

13. The assembly according to claim 9, wherein the at least one temperature sensor comprises a first temperature sensor and a second temperature sensor, the first temperature sensor is configured to output the trigger command to the one or more processors if the temperature is determined to exceed a first predefined threshold and the first temperature sensor or the second temperature sensor is configured to output the trigger command to the one or more processors if the temperature is determined to fall below a second predefined threshold.

14. The assembly according to claim 9, wherein the at least one temperature sensor comprises one of a temperature switch, a mechanical temperature sensor, an electrical temperature sensor or an integrated circuit temperature sensor.

15. The assembly according to claim 9, wherein the one or more processors is further configured to transmit documentation data to an external data processing device.

16. The assembly according to claim 15, wherein the external data processing device is a network device connected to the internet.

17. The assembly according claim 9, wherein the one or more processors is configured to analyze saved timestamps and corresponding predefined thresholds and to identify the reprocessing applied to the medical device.

18. A reusable medical device comprising the assembly according to claim 9.

19. A system for documenting a reprocessing of a reusable medical device, the system comprising:
the reusable medical device according to claim 18;
a reprocessing device for reprocessing the reusable medical device; and
an external data processing device.

* * * * *